US009714891B2

United States Patent
Liu et al.

(10) Patent No.: US 9,714,891 B2
(45) Date of Patent: *Jul. 25, 2017

(54) ROCK FIXING DEVICE WITH HYDRAULIC-SPRING COMBINATION AND POSITION-LIMITING CHUCK FOR DIRECT TENSILE TEST

(71) Applicant: Sichuan University, Chengdu (CN)

(72) Inventors: Jianfeng Liu, Chengdu (CN); Heping Xie, Chengdu (CN); Yang Ju, Chengdu (CN); Huining Xu, Chengdu (CN); Lu Wang, Chengdu (CN); Yangmengdi Xu, Chengdu (CN); Hang Zou, Chengdu (CN); Zhiwei Zhou, Chengdu (CN); Yue Zhuo, Chengdu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/015,150

(22) Filed: Feb. 4, 2016

(65) Prior Publication Data

US 2016/0231211 A1   Aug. 11, 2016

(30) Foreign Application Priority Data

Feb. 9, 2015   (CN) .......................... 2015 1 0068124

(51) Int. Cl.
*G01N 3/04* (2006.01)
*G01N 3/10* (2006.01)
*G01N 33/24* (2006.01)
*G01N 3/08* (2006.01)

(52) U.S. Cl.
CPC ................ *G01N 3/04* (2013.01); *G01N 3/08* (2013.01); *G01N 3/10* (2013.01); *G01N 33/24* (2013.01);
(Continued)

(58) Field of Classification Search
CPC .. G01N 3/04; G01N 3/08; G01N 3/10; G01N 33/24; G01N 2203/0447;
(Continued)

(56) References Cited

U.S. PATENT DOCUMENTS 2,488,279 A * 11/1949 Fitzmaurice ........... B21D 37/10
173/131
3,182,493 A * 5/1965 Patterson .................. B22C 5/00
73/831
(Continued)

*Primary Examiner* — Jonathan Dunlap
(74) *Attorney, Agent, or Firm* — Matthais Scholl, PC; Matthias Scholl

(57) ABSTRACT

A device for fixing a rock sample, including: a lower clamp and an upper clamp; the lower clamp including a lower connector connected to a loading base at a bottom of a testing machine, a lower end cap for fixing samples, a lower chain connecting the lower connector and the lower end cap, a first spiral spring, a first central position-limit mechanism, a second central position-limit mechanism, and a first hydraulic mechanism; the upper clamp including an upper connector connected to a loading base at a top of the testing machine, an upper end cap for fixing samples, an upper chain connecting the upper connector and the upper end cap, a second spiral spring, a third central position-limit mechanism, a fourth central position-limit mechanism, and a second hydraulic mechanism.

3 Claims, 8 Drawing Sheets

(52) U.S. Cl.
CPC ............... *G01N 2203/0017* (2013.01); *G01N 2203/0048* (2013.01); *G01N 2203/0405* (2013.01); *G01N 2203/0411* (2013.01); *G01N 2203/0447* (2013.01)

(58) Field of Classification Search
CPC ... G01N 2203/0405; G01N 2203/0017; G01N 2203/0048; G01N 2203/0411
USPC .... 73/779, 856, 860, 826, 831, 781, 862.42, 73/862.392, 862.69, 788, 806, 760, 837
See application file for complete search history.

(56) References Cited

U.S. PATENT DOCUMENTS

| | | | | |
|---|---|---|---|---|
| 3,354,704 A | * | 11/1967 | Gloor | G01N 3/16 73/796 |
| 4,431,202 A | * | 2/1984 | Swenson | B23B 31/102 279/106 |
| 5,191,689 A | * | 3/1993 | Slesinski | B21J 15/046 29/243.517 |
| 5,795,257 A | * | 8/1998 | Giese | F16H 7/1218 474/109 |
| 7,624,647 B2 | * | 12/2009 | Liu | G01N 3/08 73/831 |
| 9,488,559 B2 | * | 11/2016 | Liu | G01N 3/08 |
| 9,488,560 B2 | * | 11/2016 | Liu | G01N 3/08 |
| 9,494,502 B2 | * | 11/2016 | Liu | G01N 3/08 |
| 9,500,574 B2 | * | 11/2016 | Liu | G01N 3/08 |
| 9,574,980 B2 | * | 2/2017 | Liu | G01N 3/04 |
| 2008/0276719 A1 | * | 11/2008 | Xu | G01N 3/08 73/831 |
| 2016/0231213 A1 | * | 8/2016 | Liu | G01N 3/08 |
| 2016/0231214 A1 | * | 8/2016 | Liu | G01N 3/08 |
| 2016/0231215 A1 | * | 8/2016 | Liu | G01N 3/08 |
| 2016/0231216 A1 | * | 8/2016 | Liu | G01N 3/08 |

* cited by examiner

ROCK FIXING DEVICE WITH HYDRAULIC-SPRING COMBINATION AND POSITION-LIMITING CHUCK FOR DIRECT TENSILE TEST

CROSS-REFERENCE TO RELATED APPLICATIONS

Pursuant to 35 U.S.C. §119 and the Paris Convention Treaty, this application claims the foreign priority benefit of Chinese Patent Application No. 201510068124.8 filed Feb. 9, 2015, the contents of which, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, and Cambridge, Mass. 02142.

BACKGROUND OF THE INVENTION

Field of the Invention

The invention relates to a device for conducting direct tensile test on fragile materials, and more particularly to a device for fixing a rock sample.

Description of the Related Art

Direct tensile test is typically adopted for testing tensile strength of rock samples. However, because the fixing device for fixing the rock samples has structural limits, the test results are often inaccurate and the rock samples are easily damaged during the test.

SUMMARY OF THE INVENTION

In view of the above-described problems, it is one objective of the invention to provide a device for fixing a rock sample that ensures the coincidence between the center line of the spiral spring and the center line of the testing machine and the consistence in the loading rigidity at two ends of the test sample and that makes the connection between the chains and the end caps much convenient, thus improving the efficiency.

To achieve the above objective, in accordance with one embodiment of the invention, there is provided a device for fixing a rock sample. The device comprises: a lower clamp and an upper clamp: the lower clamp consists of a lower connector connected to the loading base at the bottom of the testing machine, a lower end cap for fixing samples, a lower chain connecting the lower connector and the lower end cap, a first spiral spring, a first central position-limit mechanism, a second central position-limit mechanism and a first hydraulic mechanism, and the lower end cap consists of a first sample fixing groove and a first connection segment; and the upper clamp consists of an upper connector connected to the loading base at the top of the testing machine, an upper end cap for fixing samples, an upper chain connecting the upper connector and the upper end cap, a second spiral spring, a third central position-limit mechanism, a fourth central position-limit mechanism and a second hydraulic mechanism, and the upper end cap consists of a second sample fixing groove and a second connection segment; the first central position-limit mechanism, the second central position-limit mechanism, the third central position-limit mechanism and the fourth central position-limit mechanism have the same structure and all consist of a three-jaw chuck, a support and a connecting board; One end of the support is connected to the connecting board; and another end of the support is connected to the three-jaw chuck. The first hydraulic mechanism and the second hydraulic mechanism have the same structure, which both comprise a circular piston and a circular oil cylinder assembled with the circular piston. The first central position-limit mechanism and the loading base at the bottom of the testing machine are assembled. The three-jaw chuck in the first central position-limit mechanism contacts the loading base at the bottom of the testing machine. The lower connector is arranged in the center hole of the three-jaw chuck. Free ends of three claws of the three-jaw chuck in the first central position-limit mechanism contact the external side of the lower connector respectively. The second central position-limit mechanism and the lower end cap are assembled. The three-jaw chuck in the second central position-limit mechanism contacts the outer bottom wall of the first sample fixing groove of the lower end cap. The first connection segment of the lower end cap is arranged in the center hole of the three-jaw chuck. Free ends of three claws of the three-jaw chuck in the second central position-limit mechanism contact the external side of the lower end cap. The first hydraulic mechanism is integrated with the first central position-limit mechanism or the second central position-limit mechanism When the first hydraulic mechanism is integrated with the first central position-limit mechanism, the circular oil cylinder of the first hydraulic mechanism is connected to the connecting board of the first central position-limit mechanism; one end of the first spiral spring is connected to the circular piston of the first hydraulic mechanism, and another end of the first spiral spring is connected to the connecting board of the second central position-limit mechanism. When the first hydraulic mechanism is integrated with the second central position-limit mechanism, the circular oil cylinder of the first hydraulic mechanism is connected to the connecting board of the second central position-limit mechanism; one end of the first spiral spring is connected to the circular piston of the first hydraulic mechanism, and another end of the first spiral spring is connected to the connecting board of the first central position-limit mechanism. The lower chain is arranged in the space enclosed by the first central position-limit mechanism, the first hydraulic mechanism, the first spiral spring and the second central position-limit mechanism. The third central position-limit mechanism and the upper end cap are assembled. The three-jaw chuck in the third central position-limit mechanism contacts the outer bottom wall of the second sample fixing groove of the upper end cap. The second connection segment of the upper end cap is arranged in the center hole of the three-jaw chuck. Free ends of three claws in the three-jaw chuck in the third central position-limit mechanism contact the external side of the second connection segment of the upper end cap respectively. The fourth central position-limit mechanism and the loading base at the top of the testing machine are assembled. The three-jaw chuck in the fourth central position-limit mechanism contacts the loading base at the top of the testing machine. The upper connector is arranged in the center hole of the three-jaw chuck. Free ends of three claws of the three-jaw chuck in the fourth central position-limit mechanism contact the outer side of the upper connector. The second hydraulic mechanism is integrated with the third central position-limit mechanism or the fourth central position-limit mechanism. When the second hydraulic mechanism is integrated with the third central position-limit mechanism, the circular oil cylinder of the second hydraulic mechanism is connected to the connecting board of the third central position-limit mechanism; one end of the second spiral spring is connected to the circular piston of the second hydraulic mechanism, and another end of the second spiral spring is connected to the connecting board of the fourth central position-limit mechanism. When the second hydraulic mechanism is integrated with the fourth central position-limit mechanism, the circular oil cylinder of the second hydraulic mechanism is connected to the connecting board of the fourth central position-limit mechanism; one end of the second spiral spring is connected to the circular piston of the second hydraulic mechanism, and another end of the second spiral spring is connected to the connecting board of the third central position-limit mechanism. The upper chain is arranged in the space enclosed by the third central position-limit mechanism, the second hydraulic mechanism, the second spiral spring and the fourth central position-limit mechanism.

In a class of this embodiment, the supports in the first central position-limit mechanism, the second central position-limit mechanism, the third central position-limit mechanism and the fourth central position-limit mechanism are four round rods, the connecting board is a circular board, and the four round rods are all arranged on the three-jaw chuck and the circular surface of the connecting board; or, the supports in the first central position-limit mechanism, the second central position-limit mechanism, the third central position-limit mechanism and the fourth central position-limit mechanism are two board bodies with a circular arc cross section, the connecting board is a circular board, the two board bodies are arranged on the three-jaw chuck and the circular surface of the connecting board symmetrically.

In a class of this embodiment, the three-jaw chuck is selected from a manual chuck, a pneumatic chuck, or a hydraulic chuck.

Compared with existing technologies, advantages of the device for fixing rock sample are as follows:

1. Since a spiral spring and two central position-limit mechanisms are arranged on both the lower clamp and the upper clamp of the rock sample fixing device hereof, the invention can not only ensure that the loading rigidity at both ends of a sample in a test are consistent but also test the mechanical effect after rock test peak stress more effectively. Through the three-jaw chuck in the central position-limit mechanisms of the lower clamp and the upper clamp, the invention can ensure that the center line of spiral spring and the center line of the testing machine coincide in the test, avoid the occurrence of additional eccentric force and be conducive to improvement of accuracy and success rate of the test.

2. Both the upper clamp and the lower clamp are provided with the hydraulic mechanisms. When the chains and the corresponding end caps are connected, the circular pistons drive the spiral springs and the central position-limit mechanisms to move or compress the spiral springs so as to expose the connection part between the chains and the corresponding end caps. The connection between the chains and the end caps are convenient and energy saving, and the test sample is protected from damage before loading, thus improving the efficiency and ensuring the reliability of the test results.

In figures, the following reference numbers are used: 1. Loading base at a bottom of a testing machine; 2. Three-jaw chuck; 2-1. First jaw chuck; 2-2. Second jaw chuck; 2-3. Claw; 2-4. Small bevel gear; 2-5. Large bevel gear; 2-5-1. Plane threads; 2-5-2. Bevel teeth; 3. Lower connector; 4. Support; 5. Connecting board; 6. Lower chain; 7. Lower bolt; 8. Lower end cap; 9. Rock sample; 10. Upper end cap; 11. Upper bolt; 12. Upper chain; 13. Upper connecter; 14. Loading base at a top of the testing machine; 15. First spiral spring; 16. Second spiral spring; 17. Circular piston; 18. Circular oil cylinder; 19. Piston position-limit ring; 20. Sealing washer; 21. Oil pipe; and 22. Control valve.

DETAILED DESCRIPTION OF THE EMBODIMENTS

For further illustrating the invention, experiments detailing a device for fixing rock sample are described below. It should be noted that the following examples are intended to describe and not to limit the invention.

Figure 1:
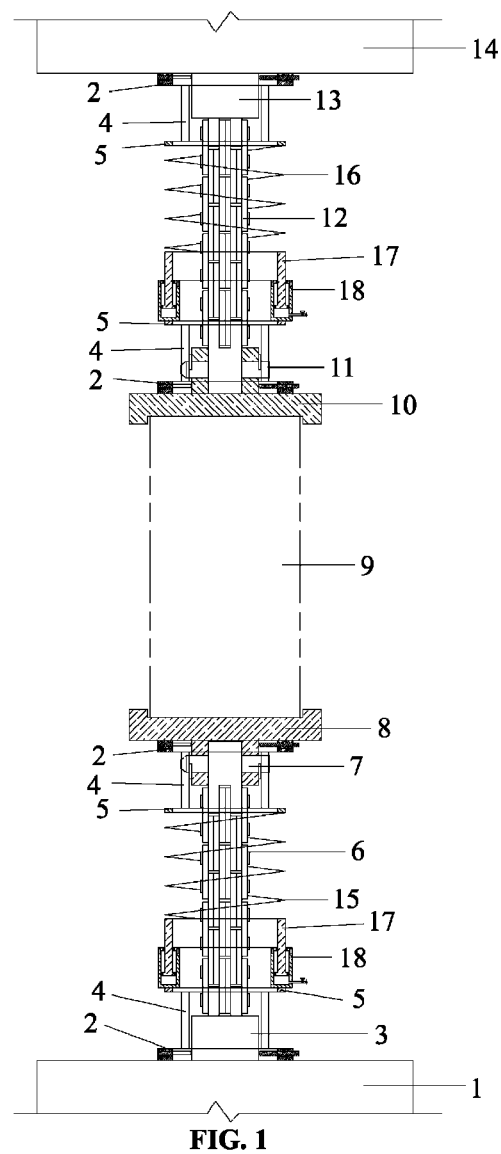
FIG. 1 is a schematic diagram of a device for fixing rock sample in accordance with one embodiment of the invention.

In the embodiment, the device for fixing rock sample consists of a lower clamp and an upper clamp as shown in the FIG. 1. The lower clamp consists of a lower connector 3 connected to the loading base 1 at the bottom of the testing machine, a lower end cap 8 for fixing samples, a lower chain 6 connecting the lower connector and the lower end cap, a first spiral spring 15, a first central position-limit mechanism, a second central position-limit mechanism and a first hydraulic mechanism, and the lower end cap 8 consists of a first sample fixing groove and a first connection segment; the first spiral spring 15 is a cylindrical compressed spiral spring; and the upper clamp consists of an upper connector 13 connected to the loading base 14 at the top of the testing machine, an upper end cap 10 for fixing samples, an upper chain 12 connecting with the upper connector and the upper end cap, a second spiral spring 16, a third central position-limit mechanism, a fourth central position-limit mechanism and a second hydraulic mechanism, and the upper end cap 10 consists of a second sample fixing groove and a second connection segment. The second spiral spring 16 is a cylindrical compressed spiral spring.

Figure 2:
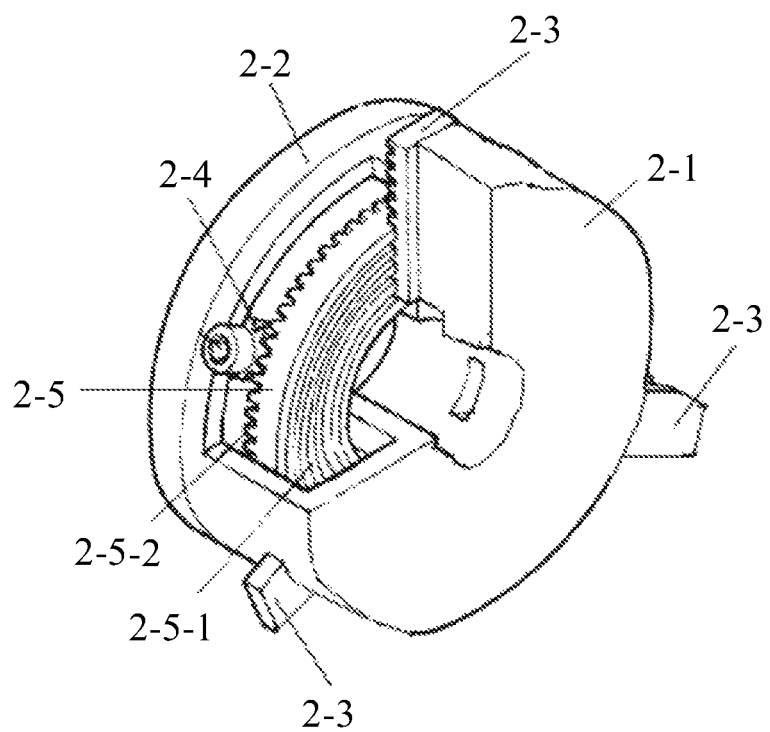
FIG. 2 is a schematic diagram of a three-jaw chuck in accordance with one embodiment of the invention.
Figure 3:
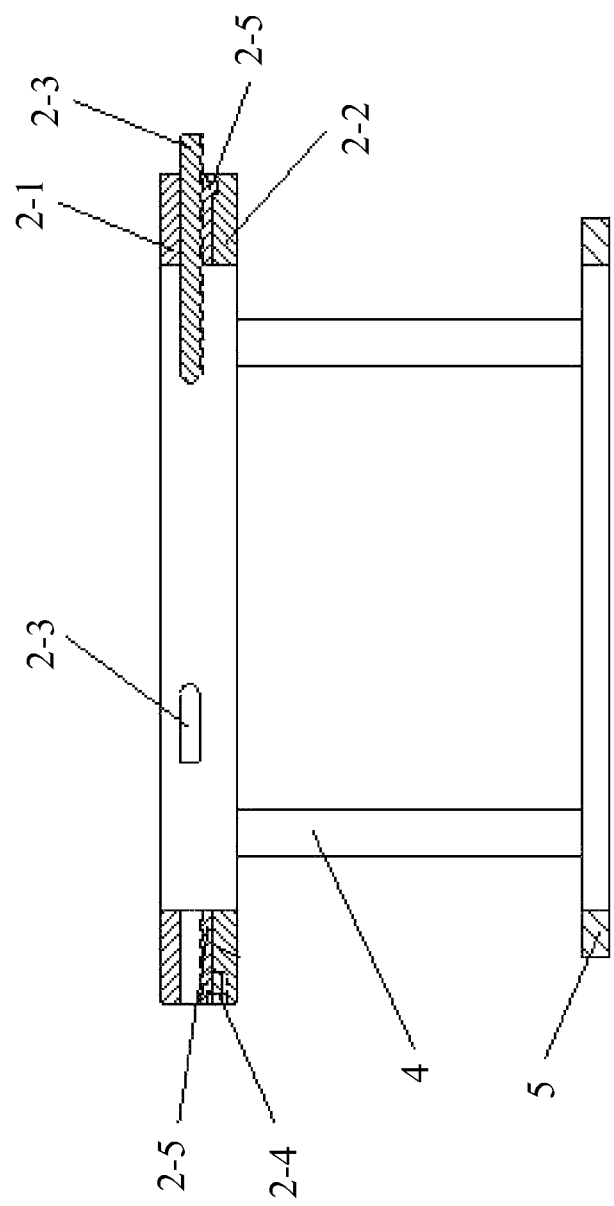
FIG. 3 is a first schematic diagram of a first central position-limit mechanism or a second central position-limit mechanism or a third central position-limit mechanism or a fourth central position-limit mechanism in a device for fixing rock sample (supports are round rods) in accordance with one embodiment of the invention.
Figure 4:
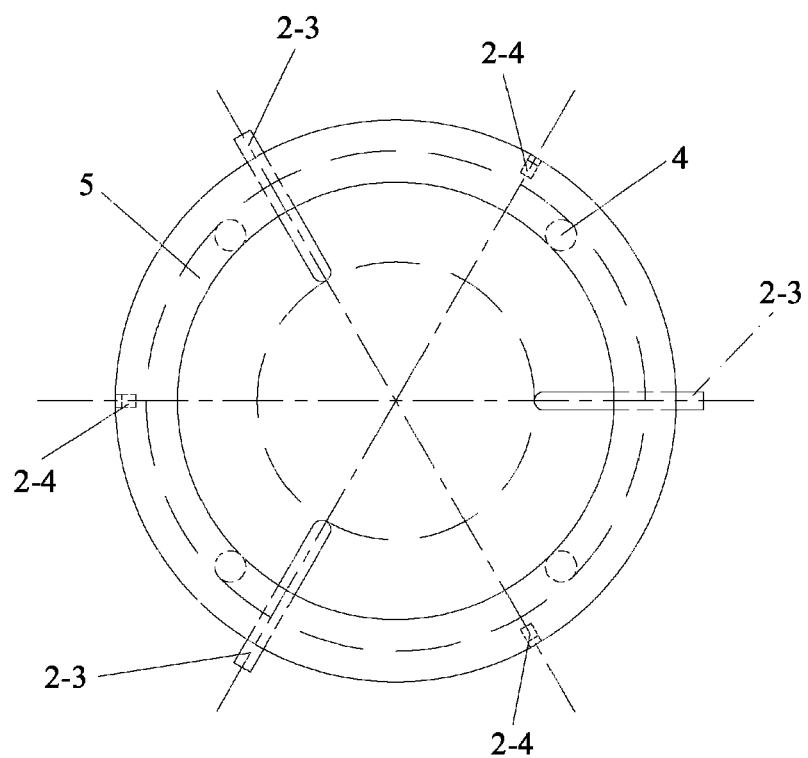
FIG. 4 is a top view of a central position-limit mechanism of a device for fixing rock sample in FIG. 3 in accordance with one embodiment of the invention.

The first central position-limit mechanism, the second central position-limit mechanism, the third central position-limit mechanism and the fourth central position-limit mechanism have the same structure and all consist of a three-jaw chuck 2, a support 4 and a connecting board 5 as shown in FIGS. 3-4. As shown in FIG. 2, the three-jaw chuck 2 is a manual chuck, and comprises a first jaw chuck 2-1, a second jaw chuck 2-2, three claws 2-3, a small bevel gear 2-4, and a large bevel gear 2-5. The first jaw chuck 2-1 and the second jaw chuck 2-2 are circular chucks, whose center hole diameters are the same. One side of the large bevel gear 2-5 is the bevel teeth 2-5-2 engaging with the small bevel gear; the plane threads 2-5-1 are arranged on the other side of large bevel gear; the threads matching the plane threads 2-5-1 are arranged on the three claws 2-3. After assembly, the small bevel gear 2-4 and the large bevel gear 2-5 are arranged in the space enclosed by the first jaw chuck 2-1 and the second jaw chuck 2-2. The three claws 2-3 are respectively arranged in three guide grooves which are distributed with an angle of 120° in the claw chuck 2-1; and the threads of the claws engage with the plane threads 2-5-1 of the large bevel gear. The supports 4 are four round rods. The connecting board 5 is a circular board, whose center hole diameter are identical with the center hole diameter of the first jaw chuck 2-1 and the second jaw chuck 2-2. The four round rods are all arranged on the first jaw chuck 2-1 and the circular surface of the connecting board 5; and one ends of the round rods are connected to the first jaw chuck 2-1.

Figure 7:
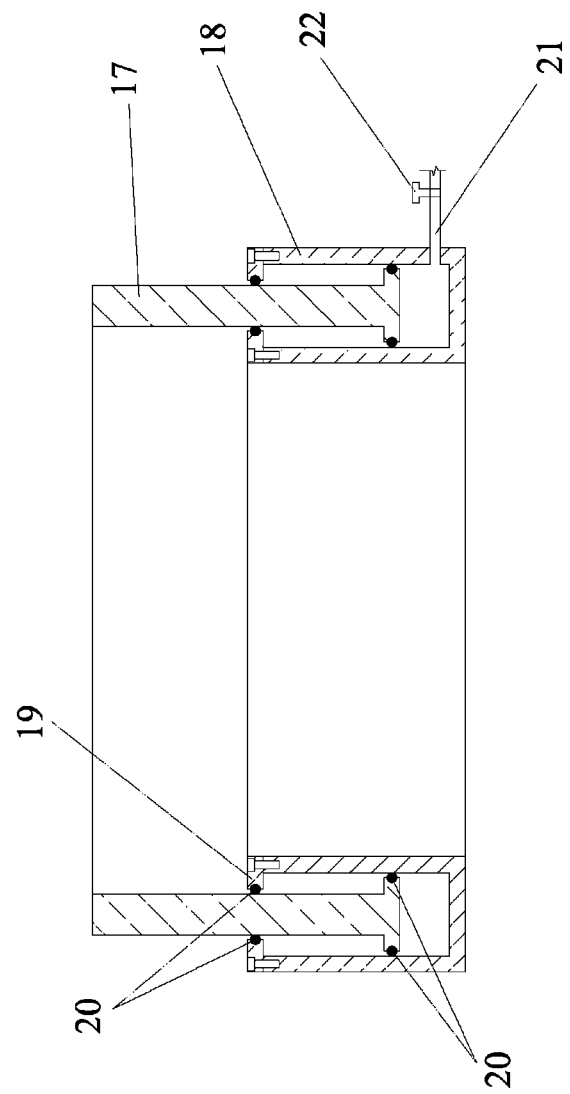
FIG. 7 is a schematic diagram of a first hydraulic mechanism in a device for fixing rock sample or the second hydraulic mechanism in accordance with one embodiment of the invention.
Figure 8:
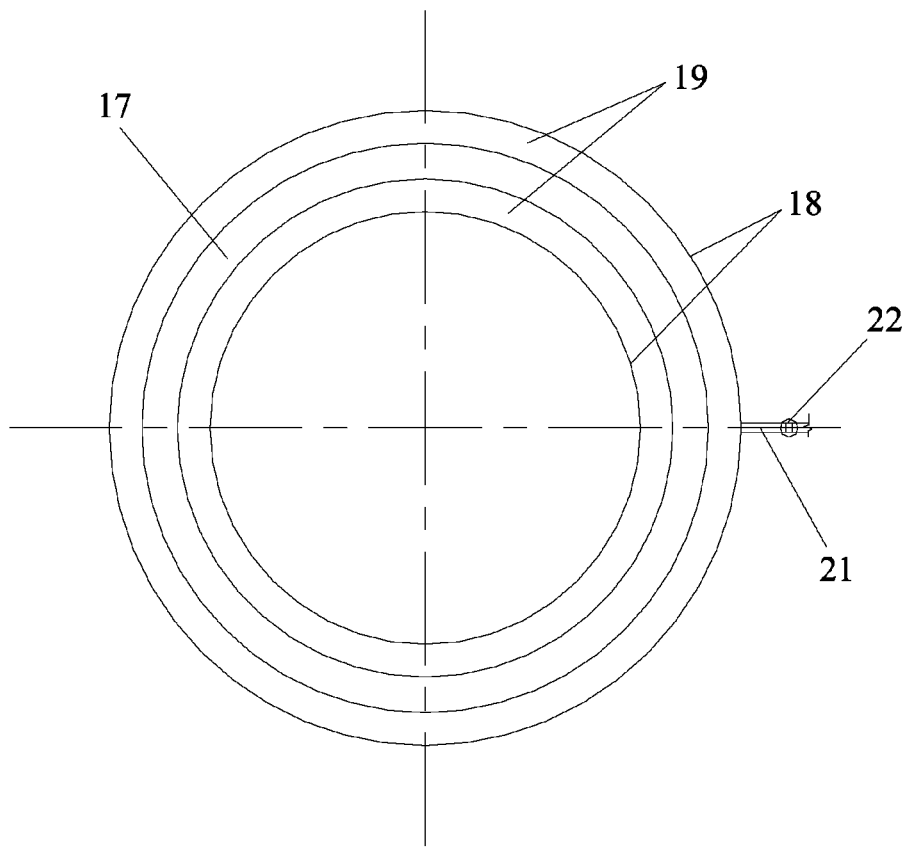
FIG. 8 is top view of a first hydraulic mechanism or a second hydraulic mechanism in FIG. 7 in accordance with one embodiment of the invention.

As shown in FIGS. 7-8, the first hydraulic mechanism and the second hydraulic mechanism both comprise a circular piston 17, a circular oil cylinder 18, a piston position-limit ring 19 and sealing washers 20. One end of the circular piston 17 is inserted into and arranged in the circular cavity of the circular oil cylinder 18. An oil pipe 21 connected to the cavity is arranged at the closed end of the circular cavity of the circular oil cylinder 18. A control valve 22 is arranged on the oil pipe 21. The piston position-limit ring 19 is arranged on the open end of the circular cavity of the circular oil cylinder 18. The sealing washers 20 are arranged on one end of the circular cavity inserted into the circular piston 17 and on the piston position-limit ring 19.

The assembly method of each member or component of the lower clamp: the first central position-limit mechanism and the loading base 1 at the bottom of the testing machine are assembled. The second jaw chuck 2-2 of the three-jaw chuck in the first central position-limit mechanism contacts the loading base 1. The lower connector 3 is arranged in the center holes of the first jaw chuck 2-1 and the second jaw chuck 2-2. Free ends of three claws of the three-jaw chuck in the first central position-limit mechanism contact the external side of the lower connector 3 respectively. The second central position-limit mechanism and the lower end cap 8 are assembled. The second jaw chuck 2-2 of the three-jaw chuck in the second central position-limit mechanism contacts the outer bottom wall of the first sample fixing groove of the lower end cap 8. The first connection segment of the lower end cap 8 is arranged in the center holes of the first jaw chuck 2-1 and the second jaw chuck 2-2. Free ends of three claws of the three-jaw chuck in the second central position-limit mechanism contact the external side of the lower end cap. The first hydraulic mechanism is integrated with the first central position-limit mechanism. The circular oil cylinder 18 of the first hydraulic mechanism is connected to the connecting board 5 of the first central position-limit mechanism; one end of the first spiral spring 15 is connected to the circular piston 17 of the first hydraulic mechanism, and another end of the first spiral spring is connected to the connecting board 5 of the second central position-limit mechanism. The lower end of the lower chain 6 is connected to the lower connector 3 arranged on the loading base 1 at the bottom of the testing machine; and a dismountable connection between the upper end of the lower chain and the lower end cap is formed by the bolt 7. The lower chain 6 is arranged in the space enclosed by the first central position-limit mechanism, the first hydraulic mechanism, the first spiral spring 15 and the second central position-limit mechanism.

The assembly method of each member or component of the upper clamp: the third central position-limit mechanism and the upper end cap 10 are assembled. The second jaw chuck 2-2 of the three-jaw chuck in the third central position-limit mechanism contacts the outer bottom wall of the second sample fixing groove of the upper end cap 10. The second connection segment of the upper end cap 10 is arranged in the center holes of the first jaw chuck 2-1 and the second jaw chuck 2-2. Free ends of three claws of the three-jaw chuck in the third central position-limit mechanism respectively contact the external side of the second connection segment of the upper end cap. The fourth central position-limit mechanism and the loading base 14 at the top of the testing machine are assembled. The second jaw chuck 2-2 of the three-jaw chuck in the fourth central position-limit mechanism contacts the loading base 14 at the top of the testing machine. The upper connector 13 is arranged in the center holes of the first jaw chuck 2-1 and the second jaw chuck 2-2. Free ends of three claws of the three-jaw chuck in the fourth central position-limit mechanism respectively contact the outer side of the upper connector 13. The second hydraulic mechanism is integrated with the third central position-limit mechanism The circular oil cylinder 18 of the second hydraulic mechanism is connected to the connecting board 5 of the third central position-limit mechanism; one end of the second spiral spring 16 is connected to the circular piston 17, of the second hydraulic mechanism, and another end of the second spiral spring 16 is connected to the connecting board 5 of the fourth central position-limit mechanism. The upper end of the upper chain 12 is connected to the upper connector 13 arranged on the loading base 14 at the top of the testing machine; a dismountable connection between the lower end of the upper chain and the upper end cap is formed by the bolt 11. The upper chain 12 is arranged in the space enclosed by the third central position-limit mechanism, the second hydraulic mechanism, the second spiral spring 16 and the fourth central position-limit mechanism.

The rock sample 9 is arranged as shown in the FIG. 1. Both ends of the rock sample are connected to the second sample fixing grooves of the upper end cap 10 and the lower end cap 8 by high-strength adhesive.

Figure 5:
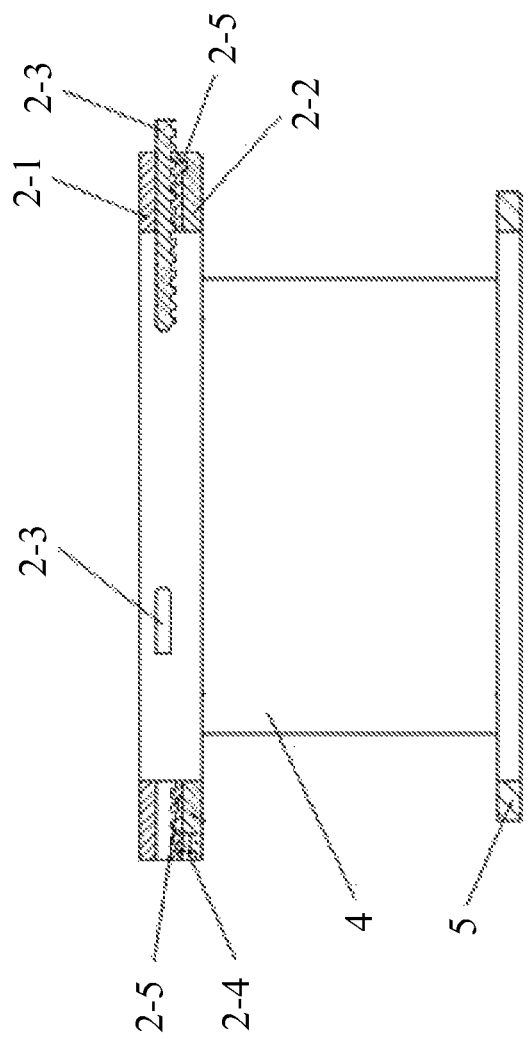
FIG. 5 is a second schematic diagram of a first central position-limit mechanism or a second central position-limit mechanism or a third central position-limit mechanism or a fourth central position-limit mechanism in a device for fixing rock sample (the supports are arc board bodies) in accordance with one embodiment of the invention.
Figure 6:
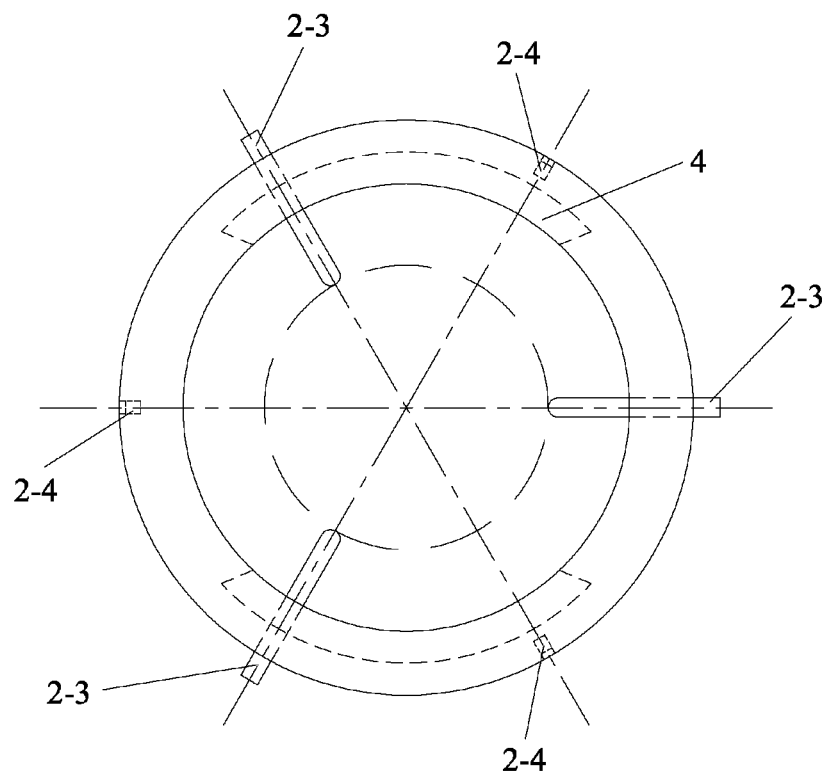
FIG. 6 is a top view of a central position-limit mechanism of a device for fixing rock sample in FIG. 5 in accordance with one embodiment of the invention.

The invention is not limited to the embodiment. For example, the first central position-limit mechanism, the second central position-limit mechanism, the third central position-limit mechanism and the fourth central position-limit mechanism can also have the structure shown in FIGS. 5-6. That is, the supports 4 are two board bodies with a circular arc cross section; the connecting board 5 is a circular arc board; the two board bodies are arranged on the first jaw chuck 2-1 and the circular surface of the connecting board 5 symmetrically; one ends of the two board bodies are connected to the connecting board 5; the other ends of the two board bodies are connected to the first jaw chuck 2-1. The three-jaw chuck could also be a pneumatic chuck, or a hydraulic chuck.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A device for fixing a rock sample, the device comprising:
   a lower clamp; the lower clamp comprising: a lower connector connected to a loading base at a bottom of a testing machine, a lower end cap for fixing samples comprising a first sample fixing groove and a first connection segment, a lower chain connecting the lower connector and the lower end cap, a first spiral spring, a first central position-limit mechanism, a second central position-limit mechanism, and a first hydraulic mechanism; and
   an upper clamp; the upper clamp comprising: an upper connector connected to a loading base at a top of the testing machine, an upper end cap for fixing samples comprising a second sample fixing groove and a second connection segment, an upper chain connecting the upper connector and the upper end cap, a second spiral spring, a third central position-limit mechanism, a fourth central position-limit mechanism, and a second hydraulic mechanism;
   wherein
   the first central position-limit mechanism, the second central position-limit mechanism, the third central position-limit mechanism and the fourth central position-limit mechanism have the same structure and all comprise a three-jaw chuck, a support and a connecting board; one end of the support is connected to the connecting board; and another end of the support is connected to the three-jaw chuck;
   the first hydraulic mechanism and the second hydraulic mechanism have the same structure, which both comprise a circular piston and a circular oil cylinder assembled with the circular piston;
   the first central position-limit mechanism and the loading base at the bottom of the testing machine are assembled; the three-jaw chuck in the first central position-limit mechanism contacts the loading base at the bottom of the testing machine; the lower connector is arranged in a center hole of the three-jaw chuck; free ends of three claws of the three-jaw chuck in the first central position-limit mechanism contact the external side of the lower connector respectively; the second central position-limit mechanism and the lower end cap are assembled; the three-jaw chuck in the second central position-limit mechanism contacts an outer bottom wall of the first sample fixing groove of the lower end cap; the first connection segment of the lower end cap is arranged in the center hole of the three-jaw chuck; free ends of three claws of the three-jaw chuck in the second central position-limit mechanism contact an external side of the lower end cap;
   the first hydraulic mechanism is integrated with the first central position-limit mechanism or the second central position-limit mechanism; when the first hydraulic mechanism is integrated with the first central position-limit mechanism, the circular oil cylinder of the first hydraulic mechanism is connected to the connecting board of the first central position-limit mechanism; one end of the first spiral spring is connected to the circular piston of the first hydraulic mechanism, and another end of the first spiral spring is connected to the connecting board of the second central position-limit mechanism; when the first hydraulic mechanism is integrated with the second central position-limit mechanism, the circular oil cylinder of the first hydraulic mechanism is connected to the connecting board of the second central position-limit mechanism; one end of the spiral spring is connected to the circular piston of the first hydraulic mechanism, and another end of the first spiral spring is connected to the connecting board of the first central position-limit mechanism; the lower chain is arranged in a space enclosed by the first central position-limit mechanism, the first hydraulic mechanism, the first spiral spring and the second central position-limit mechanism;
   the third central position-limit mechanism and the upper end cap are assembled; the three-jaw chuck in the third central position-limit mechanism contacts the outer bottom wall of the second sample fixing groove of the upper end cap; the second connection segment of the upper end cap is arranged in the center hole of the three-jaw chuck; free ends of three claws of the three-jaw chuck in the third central position-limit mechanism contact the external side of the second connection segment of the upper end cap respectively; the fourth central position-limit mechanism and the loading base at the top of the testing machine are assembled; the three-jaw chuck in the fourth central position-limit mechanism contacts the loading base at the top of the testing machine; the upper connector is arranged in the center hole of the three-jaw chuck; free ends of three claws of the three-jaw chuck in the fourth central position-limit mechanism contact the outer side of the upper connector;
   the second hydraulic mechanism is integrated with the third central position-limit mechanism or the fourth central position-limit mechanism; when the second hydraulic mechanism is integrated with the third central position-limit mechanism, the circular oil cylinder of the second hydraulic mechanism is connected to the connecting board of the third central position-limit mechanism; one end of the second spiral spring is connected to the circular piston of the second hydraulic mechanism, and another end of the second spiral spring is connected to the connecting board of the fourth central position-limit mechanism; when the second hydraulic mechanism is integrated with the fourth central position-limit mechanism, the circular oil cylinder of the second hydraulic mechanism is connected to the connecting board of the fourth central position-limit mechanism; one end of the second spiral spring is connected to the circular piston of the second hydraulic mechanism, and another end of the second spiral spring is connected to the connecting board of the third central position-limit mechanism; the upper chain is arranged in a space enclosed by the third central position-limit mechanism, the second hydraulic mechanism, the second spiral spring and the fourth central position-limit mechanism.

2. The device of claim 1, wherein the supports in the first central position-limit mechanism, the second central position-limit mechanism, the third central position-limit mechanism and the fourth central position-limit mechanism are four round rods, the connecting board is a circular board, and the four round rods are all arranged on the three-jaw chuck and a circular surface of the connecting board.

3. The device of claim 1, wherein the supports in the first central position-limit mechanism, the second central position-limit mechanism, the third central position-limit mechanism and the fourth central position-limit mechanism are two board bodies with a circular arc cross section, the connecting board is a circular board, the two board bodies are arranged on the three-jaw chuck and a circular surface of the connecting board symmetrically.

* * * * *